United States Patent
Mortato et al.

(10) Patent No.: US 10,781,280 B2
(45) Date of Patent: *Sep. 22, 2020

(54) METHOD FOR PRODUCING THERMOSETTING PHENOLIC RESINS AND PHENOLIC RESINS OBTAINABLE BY THE METHOD

(71) Applicant: AVALON Industries AG, Zug (CH)

(72) Inventors: Mariangela Mortato, Basel Stadt (CH); Stefan Krawielitzki, Holzhaeusern (CH); Francois Badoux, Unteraegeri (CH); Christopher Holmes, Nunningen (CH); Masoumeh Ghorbani, Bern (CH); Marion Sanglard, Bern (CH); Reto Frei, Evilard (CH)

(73) Assignee: AVALON Industries AG, Zug (CH)

( * ) Notice: Subject to any disclaimer, the term of this patent is extended or adjusted under 35 U.S.C. 154(b) by 57 days.

This patent is subject to a terminal disclaimer.

(21) Appl. No.: 15/904,818

(22) Filed: Feb. 26, 2018

(65) Prior Publication Data

US 2018/0244824 A1    Aug. 30, 2018

(30) Foreign Application Priority Data

| Feb. 27, 2017 | (EP) | ...................................... 17158247 |
| Feb. 27, 2017 | (EP) | ...................................... 17158248 |
| Feb. 27, 2017 | (EP) | ...................................... 17158249 |

(51) Int. Cl.
*C08G 8/06* (2006.01)
*B27N 3/00* (2006.01)
(Continued)

(52) U.S. Cl.
CPC ............... *C08G 8/06* (2013.01); *B27N 1/003* (2013.01); *B27N 3/002* (2013.01); *C07D 307/50* (2013.01);
(Continued)

(58) Field of Classification Search
CPC . C08G 8/06; C08G 8/04; B27N 1/003; B27N 3/002; C08L 61/06; C08L 61/12; C09J 161/06; C09J 161/12
See application file for complete search history.

(56) References Cited

U.S. PATENT DOCUMENTS

| 2,776,948 A | 1/1957 | Snyder |
| 2,937,158 A * | 5/1960 | Snyder ............... D21C 11/0007 |
| | | 527/303 |

(Continued)

FOREIGN PATENT DOCUMENTS

| AU | 2017243162 A1 | 11/2018 |
| CN | 101544654 B | 1/2011 |

(Continued)

OTHER PUBLICATIONS

Robert-Jan van Putten et al., "Hydroxymethylfurfural, a Versatile Platform Chemical Made from Renewable Resources," 113 Chemical Reviews 1499 (2013).*

(Continued)

*Primary Examiner* — Nicholas E Hill
(74) *Attorney, Agent, or Firm* — Collard & Roe, P.C.

(57) ABSTRACT

A method for producing thermosetting phenolic resins includes the step of reacting a polycondensable phenolic compound with 5-hydroxymethylfurfural (HMF) under conditions leading to the formation of polycondensation products. The HMF includes at least one HMF oligomer, and the reaction step is carried out at pH values greater than 7 for (Continued)

more than 60 minutes. Further, thermosetting phenolic resins may be used for producing a wood composite material.

13 Claims, 2 Drawing Sheets

(51) Int. Cl.
    *C08L 61/06*         (2006.01)
    *C08G 8/04*         (2006.01)
    *C09J 161/06*      (2006.01)
    *B27N 1/00*         (2006.01)
    *C07D 307/50*      (2006.01)
    *C08L 61/12*        (2006.01)
    *B32B 21/04*        (2006.01)

(52) U.S. Cl.
    CPC ............... *C08G 8/04* (2013.01); *C08L 61/06* (2013.01); *C08L 61/12* (2013.01); *C09J 161/06* (2013.01); *B32B 21/04* (2013.01)

(56) References Cited

U.S. PATENT DOCUMENTS

| | | | | |
|---|---|---|---|---|
| 4,048,126 | A * | 9/1977 | Gibbons | C08G 8/00 |
| | | | | 525/534 |
| 4,524,164 | A * | 6/1985 | Viswanathan | C08L 97/02 |
| | | | | 156/328 |
| 4,692,478 | A * | 9/1987 | Viswanathan | C08L 97/02 |
| | | | | 524/13 |
| 9,416,030 | B2 | 8/2016 | Vyskocil et al. | |
| 2008/0207795 | A1 | 8/2008 | Henry et al. | |
| 2013/0150597 | A1* | 6/2013 | Backes | C07D 307/46 |
| | | | | 549/488 |
| 2013/0345450 | A1 | 12/2013 | Böhling et al. | |
| 2014/0371473 | A1* | 12/2014 | Blank | B01D 3/009 |
| | | | | 549/488 |
| 2015/0083358 | A1* | 3/2015 | Joke | B22C 1/224 |
| | | | | 164/527 |
| 2016/0102165 | A1* | 4/2016 | Hsieh | C08L 63/04 |
| | | | | 525/429 |

FOREIGN PATENT DOCUMENTS

| | | | |
|---|---|---|---|
| DE | 10 2014 112 240 A1 | 3/2016 | |
| WO | WO-2015123781 A1 * | 8/2015 | ............... C08J 3/24 |
| WO | 2017/168108 A1 | 10/2017 | |

OTHER PUBLICATIONS

N. Esmaeili et al., "Hydroxynnethyl Furfural-modified Urea-Formaldehyde Resin: Synthesis and Properties," 75 European Journal of Wood Products 71 (2017), published online Jun. 24, 2016.*
Alice Mija et al., "Humins as Promising Material for Producing Sustainable Carbohydrate-derived Building Materials," 139 Construction and Building Materials 594 (2017), available online Nov. 9, 2016.*
Esmaeili, N. et al. "Hydroxymethyl furfural-modified urea-formaldehyde resin: synthesis and properties" Published online Jun. 24, 2016, Eur. J. Wood Prod., DOI 10.1007/s0017-016-1072-8, 10 pages.
European Office Action in EP 17158247.1-1302, dated Jun. 13, 2017, with English translation of relevant parts.
European Office Action in EP 17158248.9-1302, dated Jun. 14, 2017, with English translation of relevant parts.
European Office Action in EP 17158249.7-1302, dated Jun. 8, 2017, with English translation of relevant parts.
Wikipedia, "Phenol formaldehyde resin," retrieved Feb. 22, 2018, pp. 1-4 https://en.wikipedia.org/wiki/Phenol_formaldehyde_resin.
Patil et al., "Comparison of Structural Features of Humins Formed Catalytically from Glucose, Fructose, and 5-Hydroxymethylfurfuraldehyde", Energy & Fuels, American Chemical Society, 2012, pp. 5281-5293 (13 pages).
Filiciotto et al., "Benign-by-design preparation of humin-based iron oxide catalytic nanocomposites", Green Chemistry, The Royal Society of Chemistry, 19, published on Aug. 9, 2017, pp. 4423-4434 (12 pages).
Licsandru et al., "From Biorefinery By-Product to Bioresins. Thermosets Based on Humins and Epoxidized Linseed Oil", Cellulose Chemistry and Technology, 53 (9-10), 2019, pp. 963-969 (7 pages).
Speltini et al., "Sunlight-promoted photocatalytic hydrogen gas evolution from water-suspended cellulose: a systematic study", Photochemical & Photobiological Sciences, The Royal Society of Chemistry and Owner Societies, 13, published on Jun. 30, 2014, pp. 1410-1419 (10 pages).
Wang et al., Potential neurotoxicity of 5-hydroxymethylfurfural and its oligomers: widespread substances in carbohydrate-containing foods, Food & Function, Royal Society of Chemistry, Published Apr. 3, 2020, 8 pages.
Xu et al., Structural differences of the soluble oligomers and insoluble polymers from acid-catalyzed conversion of sugars with varied structures, Elesevier, Carbohydrate Polymers 216 (2019) pp. 167-179.
Fu et al., Suppression of Oligomer Formation in Glucose Dehydration by CO2 and Tetrahydrofuran, Green Chemistry, Published Jun. 6, 2017, 11 pages.
Chang et al., Synthesis of biomass-derived feedstocks for the polymers and fuels industries from 5-(hydroxymethyl) furfural (HMF) and acetone, Green Chemistry, Published Aug. 7, 2019, 10 pages.

* cited by examiner

METHOD FOR PRODUCING THERMOSETTING PHENOLIC RESINS AND PHENOLIC RESINS OBTAINABLE BY THE METHOD

Applicant claims priority under 35 U.S.C. § 119 of European Application Nos. 17158247.1, 17158248.9, and 17158249.7 all filed Feb. 27, 2017, the disclosures of which are incorporated by reference.

BACKGROUND OF THE INVENTION

1. Field of the Invention

The present invention relates to a method for producing thermosetting phenolic resins as well as thermosetting phenolic resins. In particular, the invention relates to a method for producing thermosetting phenolic resins, comprising at least one polycondensation product obtained by polycondensation of phenolic compounds with HMF and thermosetting phenolic resins obtainable by the method. The invention also relates to the use of the thermosetting phenolic resins for the production of plywood, wood fiber composite, chipboard or multilayer boards.

2. Description of the Related Art

Thermosetting resins are preferably obtained by the polycondensation of phenolic compounds and/or aminoplast formers with reactive carbonyl compounds, in particular aldehydes. By way of example, amino resins with the aminoplast formers urea, melamine and dicyandiamide, phenolic resins or amino-phenolic resins may be mentioned. The resins are generally characterized by good processing properties such as high reactivity. A duroplastic material is obtained by a subsequent curing of the resins.

For the production of wood composites, the resins are usually mixed with crushed wood, such as wood shavings or wood fibers, after which they are pressed at elevated temperatures, wherein the resins cure with crosslinking.

Due to its high reactivity, predominantly formaldehyde is used for the polycondensation. To promote the implementation, the process is often carried out with an excess of formaldehyde, so that the resins have a high content of free formaldehyde. The formaldehyde emission of the resins is therefore high.

A disadvantage here is the health risk emanating from formaldehyde, so that the use of formaldehyde is also increasingly regulated.

Due to the hazard potential, efforts have been made for years to reduce the content of formaldehyde. One measure in this case is to replace formaldehyde in the preparation of the resins by other reactive compounds. 5-hydroxymethylfurfural (HMF) has already been identified as a promising candidate for it, as it has an ability to form cross-linking bonds, is heavy-volatile and practically non-toxic, and can be obtained from renewable resources.

In the journal European Journal of Wood Products, an HMF-modified urea-formaldehyde resin is described, in the production of which up to about 30% by weight of the formaldehyde has been replaced by purified, crystalline HMF (N. Esmaeili et al., DOI 10.1007/s0017-016-1072-8). Chipboard produced with this resin exhibits an internal bond (IB) of ≥0.35 N/mm$^2$, which is currently required to meet the minimum standard for indoor slabs according to the European standard NEN EN 319. The disadvantage, however, is that the resin and chipboard produced therefrom still contain significant amounts of toxic formaldehyde.

U.S. Pat. No. 2,776,948 A discloses the production of synthetic resins based on HMF and phenolic compounds. The HMF used in this case is present in a hydrolyzate, which was prepared from hexose-containing material such as acid-impregnated wood by steam pressure hydrolysis. To cure the synthetic resins or for the production of fiberglass mats, the synthetic resins are in turn added toxic formaldehyde.

The U.S. Pat. No. 4,524,164 A describes formaldehyde-free, thermosetting resins which serve as a binder for lignocellulosic material for the production of plywood and chipboard. First, sugar-containing solutions are converted to a liquid, fusible resin under acidic conditions and in the presence of a metal catalyst at temperatures of 50° C. to 200° C. Phenolic compounds or urea are added as the crosslinking agent for the sugar and sugar degradation products. The disadvantage is that resins prepared under these conditions are made thermosetting only by the addition of a curing agent.

SUMMARY OF THE INVENTION

It is accordingly the object of the present invention to eliminate the above-mentioned disadvantages.

This is achieved according to a first aspect of the present invention by a method for the production of thermosetting phenolic resins according to a first aspect of the invention. In another aspect, the present invention relates to a thermosetting phenolic resin obtainable by the method. According to a further aspect, the present invention relates to the use of the resin according to the invention for the production of a wood composite material.

BRIEF DESCRIPTION OF THE DRAWINGS

Further advantages and advantageous embodiments are given in the claims and the following drawings, wherein:

DETAILED DESCRIPTION OF THE PREFERRED EMBODIMENTS

Figure 1:
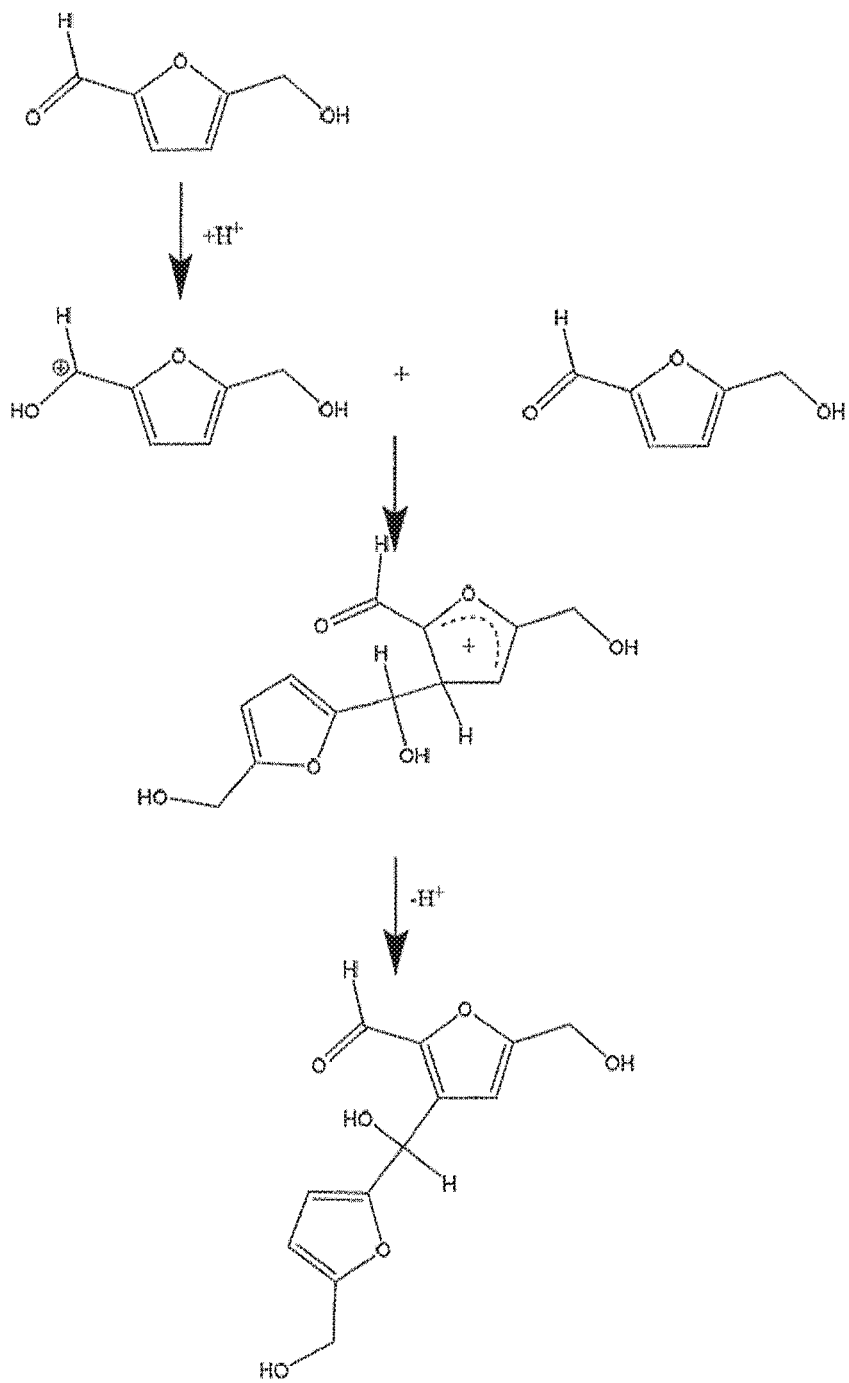
FIG. 1 shows a proposed mechanism of carbon-carbon bond formation under acidic conditions based on the dimerization of two HMF molecules, as well as FIG. 2 shows a proposed mechanism of carbon-carbon bond formation under basic conditions by dimerization of two HMF molecules.

The method for the production of thermosetting phenolic resins includes the step of reacting a polycondensable phenolic compound with 5-hydroxymethylfurfural (HMF) under conditions leading to the formation of polycondensation products and is characterized in that the HMF comprises at least one HMF oligomer, and the reaction step is carried out at pH Values of over 7 for more than 60 minutes.

It has been found that under the conditions according to the invention, formaldehyde and curing agents can be completely dispensed with both in the production and further processing of the phenolic resins and thermosetting phenolic resins can be obtained which have a bonding strength comparable to phenol-formaldehyde resins, if HMF containing HMF oligomers is used for polycondensation.

The occurrence of water-soluble linear and branched HMF oligomers in solutions of HMF is known, for example, from DE 10 2014 112 240 A1. The HMF oligomers are formed, inter alia, in the production of HMF from carbohydrates and carbohydrate-containing biomass under hydrothermal conditions and can be detected by NMR, IR and mass spectroscopy. The formation of the HMF oligomers can also be monitored, for example, by means of HPLC analyzes.

In the context of the present invention, HMF oligomers are, in contrast to HMF monomers, compounds of at least two linked HMF units/monomers. HMF oligomers are usually understood to be compounds having a molecular weight of up to 3000 g/mol. Particularly suitable for the method are HMF oligomers with low molecular weight which are soluble or at least present in a dispersed manner in the chosen solvent under the chosen reaction conditions. The transition between dissolved and dispersed form may be fluent, so that no distinction is made in this regard in the present invention.

Previously known oligomeric compounds from HMF result from the linking of aldehyde and/or hydroxyl groups of individual HMF monomers or individual monomers with HMF oligomers consisting of HMF monomers. Finally, the HMF monomers represent the units of the HMF oligomers formed. The HMF oligomers are linear, more or less heavily branched and comprise ether, hemi-acetal and/or acetal bonds. HMF oligomers are formed under both acidic and basic conditions.

Linear HMF oligomers typically contain structural units which comprise units of the type

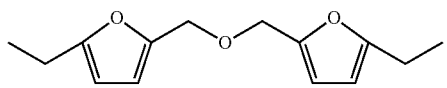

which are linked by ether bonds and/or units of the type

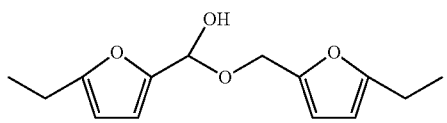 [SMILES: CCc1ccc(COC(O)c2ccc(CC)o2)o1]

which are linked by the formation of hemiacetals. Branched HMF oligomers may also contain structural elements with units of the type

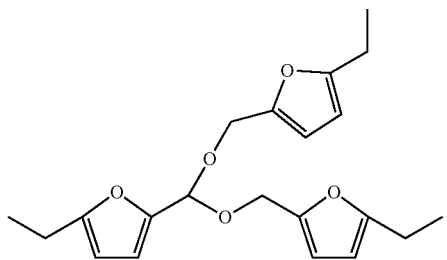 [SMILES: CCc1ccc(COC(OCc2ccc(CC)o2)c2ccc(CC)o2)o1]

which are linked by the formation of acetals. The curved lines indicate that the structural elements shown here are a section of an HMF oligomer. An HMF oligomer usually has several identical or different structural elements of the types indicated. Terminal HMF units are limited by aldehyde or hydroxymethyl groups.

It is obvious to a person skilled in the art that the at least one HMF oligomer can be present in a mixture of HMF oligomers of different lengths and/or different degrees of crosslinking. It is also possible, by selecting an HMF oligomer or by selecting a combination of different HMF oligomers, to tailor the properties of the resulting phenolic resin specifically to the technical purpose.

The polycondensation is carried out in a conventional manner. Suitable solvents for the reaction are generally known to the person skilled in the art. According to the invention, suitable solvents are understood as meaning any liquid agents in which polycondensation products can form. The reaction is preferably carried out in an aqueous solvent. In particular, the reaction step can be carried out in water.

The alkaline pH can be adjusted by suitable bases at the beginning of the reaction step. Without wishing to limit the scope of the invention, alkali hydroxides, alkaline earth hydroxides, sodium carbonate, ammonia and tertiary amines are mentioned as suitable bases by way of example, wherein sodium hydroxide in particular is suitable for adjusting the alkaline pH value.

It has been found that reaction times in the reaction step of over 60 minutes at basic pH values with an HMF having at least one HMF oligomer lead to phenolic resins which have a high bonding strength.

Said reaction step is preferably carried out for such a time until the solution has reached a desired viscosity or the reaction is complete. Desired viscosities are usually between 100 mPa·s and 1200 mPa·s. It is further preferred to carry out the reaction step until the solution has reached a viscosity of more than 200 mPa·s, particularly preferably until the solution has a viscosity of more than 800 mPa·s, more particularly preferably until the solution has a viscosity of more than 850 mPa·s.

According to an advantageous embodiment of the method, the reaction step is carried out at pH values of 7.5 to 14, preferably at pH values of 9 to 14, more preferably at pH values of 9.5 to 13, particularly preferably at pH values of 9.5 to 12.5, more particularly preferably at values of 9.8 to 12.

According to a further advantageous embodiment of the method, the reaction step is carried out for more than 60 minutes to 15 hours, for 65 minutes to 15 hours, for 80 minutes to 15 hours, for 100 minutes to 10 hours. More preferably, the reaction step is carried out for 2 to 7 hours, particularly preferably for 3 to 7 hours, especially 5 to 6.5 hours, more particularly preferably for 5 hours to 6 hours.

According to a further advantageous embodiment of the method, the reaction step is carried out at temperatures in the range of 40° C. to 170° C., preferably in the range of 50° C. to 150° C., more preferably in the range of 60° C. to 110° C., particularly preferably in the range from 70° C. to 110° C., more particularly preferably in the range of 85° C. to 110° C. In principle, the temperature for carrying out the method can be varied within a wide range. However, it has been observed that the reaction proceeds very slowly at temperatures below 40° C. If temperatures of more than 60° C. are used, the reaction is much faster. This was unexpected, as it was previously assumed that from temperatures above 50° C., an increasing decomposition of HMF takes place.

According to a further advantageous embodiment of the method, the reaction step is performed in at least two stages, wherein a first stage of the reaction step is carried out at temperatures in the range of 40° C. to 80° C., and a further stage of the reaction step is carried out at Temperatures, which are higher than the temperatures of the first stage. A multi-stage implementation of the method is advantageous from an economic point of view. It has been observed that the reaction step can be carried out in an early phase at a lower temperature than in a later phase. As a result, a lower heating in the first stage of the reaction step is sufficient and phenolic resins are obtained with a very good bonding strength. A two-stage implementation of the method is preferred.

According to a further advantageous embodiment of the method, the reaction step is carried out in a first stage for 50 to 100 minutes at temperatures in the range of 40° C. to 80° C. and in a second stage for 15 minutes to 14 hours at temperatures in the range of 85° C. up to 170° C. Preferably, the reaction step is carried out in the first stage in the range of 50° C. to 75° C., more preferably in the range of 60° C. to 68° C., particularly preferably in the range of 63° C. to 67° C., more particularly preferably at a temperature up to 65° C. The reaction step in the first stage is preferably carried out for 50 to 90 minutes, more preferably for 50 to 80 minutes, particularly preferably for 55 to 70 minutes. The reaction step in the second stage is preferably carried out at temperatures in the range from 85° C. to 150° C., more preferably from 85° C. to 110° C., particularly preferably from 85 to 100° C., more particularly preferably from 87° C. to 93° C., especially preferably at 90° C. The reaction step in the second stage is preferably carried out for 60 minutes to 7 hours, more preferably for 3 to 6 hours, particularly preferably for 3.5 to 5.5 hours, more particularly preferably for 4.5 to 5.5 hours.

According to a further advantageous embodiment of the method, the molar ratio of the amount of HMF used to the total amount of phenolic compound is 0.5:1 to 4:1, preferably the molar ratio is 1.3:1 to 3:1, more preferably the molar ratio is 1:1 to 2.7:1, particularly preferably the molar ratio is 1.5:1 to 2.6:1, more particularly preferably 2:1 to 2.5:1. In principle, the molar ratio of the amount of HMF used to the total amount of phenolic compound can be varied over a wide range. A molar excess of HMF is particularly advantageous because it can reduce the content of residual monomers of the phenolic compound in the phenolic resin. A molar ratio which is suitable for the particular phenolic compound for carrying out the method according to the invention can easily be calculated for the person skilled in the art on the basis of the molar mass of HMF (126.11 g/mol) by using the molar mass as the basis for calculation, without taking into account which proportion of the amount of HMF is actually present as a monomer or incorporated into HMF oligomers.

According to a further advantageous embodiment of the method, the proportion of HMF oligomer is 0.05% by weight to 10% by weight, based on the total amount of HMF used, preferably the proportion of HMF oligomer is 0.1% by weight to 8% by weight, based on the total amount of HMF used, particularly preferably the proportion of HMF oligomer is 2% by weight to 4% by weight, based on the total amount of HMF used. Even small amounts of HMF oligomer are sufficient to provide, under the conditions according to the invention, phenolic resins which have a bonding strength comparable to phenol-formaldehyde resins. It is obvious to the person skilled in the art that higher proportions of HMF oligomer can also be used. Also included in the invention is that the HMF oligomer is up to or close to 100% by weight, based on the total amount of HMF employed.

According to a further advantageous embodiment of the method, the HMF oligomer has 2 to 20 units, preferably 2 to 10 units, particularly preferably to 2 to 4 units. HMF oligomers having from 2 to 10 units are readily soluble in water under moderate conditions, i.e. at room temperature and under normal pressure, so that the HMF oligomers can be used without problems for polycondensation in an aqueous medium. HMF oligomers of 2 to 4 units have improved water solubility. HMF oligomers with 2 units are particularly soluble in water.

The polycondensable phenolic compound may be those commonly used for the production of thermosetting phenolic resins.

Suitable polycondensable phenolic compounds are in principle all hydroxyl-group-bearing aromatic compounds which have at least one carbon atom in the aromatic which is suitable for a nucleophilic addition reaction between the phenolic compound and the HMF.

Advantageously, the polycondensable phenolic compound is phenol, lignin, a lignin-derived phenolic compound, resorcinol, hydroquinone, hydroxyhydroquinone, catechol, phloroglucinol or a mixture of at least two of these compounds.

In addition to the components mentioned, it is also possible in this case for further phenolic compounds and/or aminoplast formers to be present. Suitable aminoplast formers are urea, melamine, substituted melamine, substituted urea, acetylenediurea, guanidine, thiourea, thiourea derivative, diaminoalkane, diamidoalkane or a mixture of at least two of these aminoplast formers.

According to a further preferred embodiment of the method, the HMF oligomer used for the polycondensation is a carbon-linked HMF oligomer.

For the purposes of the present invention, HMF oligomers are referred to as carbon-linked HMF oligomers, provided that at least two HMF units are linked to one of the two HMF units via a carbon-carbon bond involving an aromatically bonded carbon atom at position 3 or 4 of the furan ring. In particular, the carbon-linked HMF oligomer contains at least one first unit whose aldehyde group carbon atom is linked to an aromatic-bonded carbon atom of the furan ring of a second unit.

The inventors have discovered that, in addition to HMF oligomers resulting from the linking of aldehyde and/or hydroxyl groups of the HMF units and having the corresponding ether, hemiacetal and/or acetal bonds, HMF oligomers are formed both under acidic and basic conditions in which units are linked via a carbon-carbon bond. These bonds may arise, for example, upon electrophilic attack of an aldehyde group of a first HMF monomer or an HMF unit of an HMF oligomer on the carbon atom in position 3 or 4 of a furan ring of a second HMF monomer or an HMF unit of an HMF oligomer.

Figure 2:
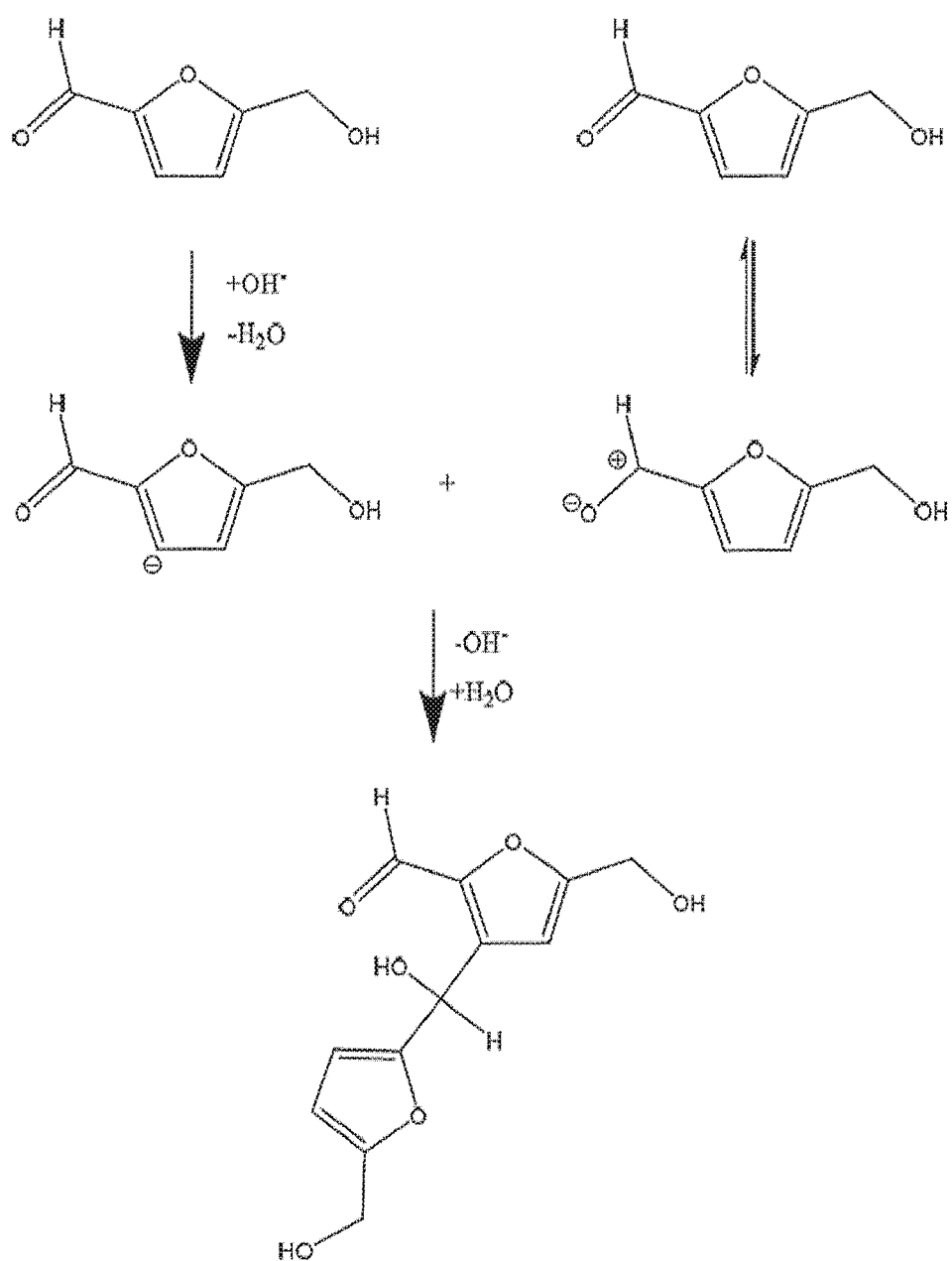

The mechanisms proposed for HMF oligomer formation in acidic and basic can be seen in FIGS. 1 and 2. From these it is apparent, inter alia, that HMF oligomers having a linkage through a carbon-carbon bond, at the same time also have more free functional aldehyde and/or hydroxyl groups than HMF oligomers in which the compound is formed only via aldehyde and/or hydroxyl groups of the HMF. This results in very reactive HMF oligomers, which have additional crosslinking options.

In the carbon-linked HMF oligomer, other bonds such as ether, hemiacetal, and/or acetal bonds may be included in addition to the bond linked with the inclusion of an aromatically bonded carbon. To increase the reactivity of the resulting phenolic resin, it is sufficient if two of the HMF units are already linked with the inclusion of an aromatically bound carbon. In particular, carbon-linked HMF oligomers with 2 units contain a comparatively high proportion of free reactive functional groups per HMF oligomer. The carbon-linked HMF oligomer may also have multiple such carbon-carbon linkages.

Furthermore, in addition to the carbon-linked HMF oligomers, further HMF oligomers having ether, hemiacetal and/or acetal bonds may be included. Due to the high proportion of free functional groups, even small amounts of carbon-linked HMF oligomer are sufficient to provide very reactive oligomers. It is also encompassed by the invention that the carbon-linked HMF oligomer is up to or close to 100% by weight, based on the total amount of HMF oligomer.

According to a further advantageous embodiment of the method, the method contains at least one further step, which provides 5-hydroxymethylfurfural, which comprises at least one HMF oligomer, for the reaction step.

The providing step preferably includes that a solution containing HMF monomers and/or HMF oligomers is subjected to conditions which lead to the formation of HMF oligomers. The inventors have found that aqueous HMF solutions, which for example are made of crystalline HMF with water, age under formation of HMF oligomers. The amount and the molecular weight of the HMF oligomers can be determined in this case by analytical means familiar to the person skilled in the art, such as HPLC and NMR spectroscopy.

The formation of HMF oligomers under moderate conditions, i.e. under normal pressure and room temperature, can be in the range of hours, days or weeks.

Particularly preferably, the conditions to which the HMF solution is subjected include alkalization or acidification of the solution. Likewise particularly preferably, the conditions include heating the solution, optionally in combination with acidification or alkalization, and/or solvent removal, such as may be carried out for example by means of a rotary evaporator under reduced pressure for concentration. Acidification, alkalization, concentration and heating can accelerate the aging process.

A particularly preferred variant of the providing step comprises providing 5-hydroxymethylfurfural, which comprises at least one HMF oligomer, by treating an aqueous suspension of cellulose-containing biomass and/or an aqueous carbohydrate solution of at least one hexose and/or one aqueous 5-hydroxymethylfurfural solution under hydrothermal conditions.

The treatment of biomass such as vegetable raw materials, of carbohydrates or of compounds derived from carbohydrates under hydrothermal conditions for obtaining 5-HMF (monomers) is known and envisages adding pressure and elevated temperature to the starting material in an aqueous medium. In the treatment of an aqueous suspension of cellulose-containing biomass and/or an aqueous carbohydrate solution of at least one hexose and/or an aqueous 5-hydroxymethylfurfural solution under hydrothermal conditions, HMF oligomers are formed.

Cellulosic biomass, which is often obtained as a waste product of agricultural producers, is particularly preferred because of its low cost factor. Preferred hexoses are fructose or glucose, in particular they may be fructose or mixtures of fructose and glucose.

Preferred hydrothermal conditions are saturated steam pressure and temperatures of 150° C. to 250° C. This has the advantage that the formation of HMF oligomers is completed within minutes to a few hours depending on the starting material.

Preferably, the providing step is carried out until the desired amount of HMF oligomer is reached or the reaction is complete. It is obvious for a person skilled in the art that the different variants for providing HMF, which comprises at least one HMF oligomer, can be combined in order to obtain the desired outcome. For example, the providing step can comprise a treatment under hydrothermal conditions as well as a concentration by solvent removal.

Preferably, the HMF comprising at least one HMF oligomer is present in an aqueous solution at the end of the providing step. However, other forms of HMF are suitable as well, for example, after complete removal of solvent.

It is further preferred to influence the content, the proportion of oligomer, based on the total amount of HMF, the size and/or the concentration of the oligomer or of the oligomers. The proportion and/or content of the oligomer or of the oligomers is particularly preferably influenced by subjecting the solution obtained in the procurement step to filtration on at least one filter medium. The treatment of an aqueous HMF solution after a hydrothermal carbonization is described, for example, in DE 10 2014 112 240 A1. The HMF, which comprises at least one HMF oligomer, is particularly preferably present in aqueous solution at a concentration from 25% by weight to 80% by weight at the end of the providing step, and even more preferably in a concentration of 27% by weight to 75% by weight, more particularly preferably in a concentration of 27% by weight to 73% by weight.

In another aspect, the present invention relates to a thermosetting phenolic resin obtainable by the method described above.

Preferably, the thermosetting phenolic resin comprises at least one polymer obtained by polycondensation of phenolic compounds with 5-hydroxymethylfurfural (HMF), wherein the polymer is a polycondensation product of a phenolic compound with an HMF oligomer.

For the purposes of the present invention, the term polymer is understood to mean products of the polycondensation. The polymers are usually water insoluble.

With regard to preferred phenolic compounds and optionally additional aminoplastics, reference may be made to the statements made above.

The solids content of the phenolic resin can be varied over a wide range. The solids content is at least 35% by weight. The solids content of the phenolic resin is preferably in the range from 40 to 80% by weight, more preferably in the range from 40 to 75% by weight, particularly preferably from 40 to 70% by weight.

Preferably, the molar ratio of the total HMF to the total amount of phenolic compound in the phenolic resin is 0.5:1 to 4:1, preferably the molar ratio is 1.3:1 to 3:1, more preferably the molar ratio is 1:1 to 2.7:1, particularly preferably the molar ratio is 1.5:1 to 2.6:1, more particularly preferably 2:1 to 2.5:1.

In a preferred embodiment of the phenolic resin, the polymer is a polycondensation product of a phenolic compound having a carbon-linked HMF oligomer containing at least a first HMF unit linked to an aromatically-bonded carbon of a second HMF unit.

With regard to the carbon-linked HMF oligomers, reference may be made to the statements made above.

According to a further aspect, the present invention relates to the use of the phenolic resin according to the invention for the production of a wood composite material.

The phenolic resins are particularly suitable for the production of composites of lignocellulose-containing material such as wood shavings, wood fibers or wood chips. The preparation of the wood composite materials is carried out according to the methods generally known in the art. The wood composites are obtained by contacting the lignocellulosic material with the phenolic resins and then curing the phenolic resins, which is accompanied by cross-linking.

The curing is preferably carried out by compressing the phenolic resin provided with the lignocellulose material. Usually, pressures of 1 to 30 mPa are used. In general, the compression takes place at a temperature in the range of 120° C. to 250° C. The specific temperature can be selected depending on the phenolic resin, the lignocellulose-containing material and the desired properties of the composite materials. Due to the reactivity of the phenolic resins, already a few minutes are sufficient to obtain wood-based materials with good mechanical properties. Preferably, the pressing time is in the range of 3 to 10 minutes, more preferably the pressing time is in the range of 5 to 8 minutes. A short pressing time is advantageous both from a production and economic point of view.

Advantageously, a curing agent can be completely dispensed with in the case of the phenolic resins according to the invention.

The obtained wood composite materials can finally be aftertreated for stabilization in a drying cabinet or wood dryer at temperatures in the range of 10° C. to 100° C. under controlled atmosphere. Such an atmosphere may, for example, include a relative humidity in the range of 40% to 70%.

A further advantage in the production of a wood composite material with thermosetting phenolic resins according to the invention is that the wood composite materials can be produced formaldehyde-free and based on natural, renewable raw materials and have very good resistance to moisture, in particular water vapor. Yet another advantage is that due to the reactivity of the phenolic resins short pressing times in the minute range are sufficient to obtain a wood composite material with very good mechanical properties.

The phenolic resins according to the invention are particularly suitable for use in the production of plywood, wood fiber composite, chipboard or multilayer boards.

Another advantage of the phenolic resins according to the invention is that they have a bonding strength comparable to phenol-formaldehyde resins.

All features of the invention may be essential to the invention both individually and in any combination.

What is claimed is:

1. A method for producing thermosetting phenolic resins comprising the step of
   reacting a polycondensable phenolic compound with 5-hydroxymethylfurfural (HMF) under conditions leading to the formation of polycondensation products,
   wherein the HMF comprises at least one water-soluble HMF oligomer with 2 to 10 monomer units of 5-hydroxymethylfurfural, and
   wherein the reaction step is carried out at pH values greater than 7 for more than 60 minutes.

2. The method according to claim 1, wherein the reaction step is carried out at pH values of 7.5 to 14.

3. The method according to claim 1, wherein the reaction step is carried out for more than 60 minutes to 15 hours.

4. The method according to claim 1, wherein the reaction step is carried out at temperatures in the range of 40° C. to 170° C.

5. The method according to claim 1, wherein the reaction step is performed in at least two stages, wherein a first stage of the reaction step is carried out at temperatures in the range of 40° C. to 80° C., and a further stage of the reaction step is carried out at Temperatures, which are higher than the temperatures of the first stage.

6. The method according to claim 1, wherein the reaction step is carried out in a first stage for 50 to 100 minutes at temperatures in the range of 40° C. to 80° C. and in a second stage for 15 minutes to 14 hours at temperatures in the range 85° C. to 170° C.

7. The method according to claim 1, wherein the molar ratio of the amount of the HMF used to the total amount of phenolic compound is 0.5:1 to 4:1.

8. The method according to claim 1, wherein the proportion of HMF oligomer, based on the total amount of HMF used, is 0.05% by weight to 10% by weight.

9. The method according to claim 1, wherein the HMF oligomer has 2 to 20 units.

10. The method according to claim 1, wherein the polycondensable phenolic compound is phenol, lignin, a lignin-derived phenolic compound, resorcinol, hydroquinone, hydroxyhydroquinone, catechol, phloroglucin or a mixture of at least two of these compounds.

11. The method according to claim 1, wherein the HMF oligomer is a carbon-linked HMF oligomer.

12. The method according to claim 1, wherein the method contains at least one further step, which provides 5-hydroxymethylfurfural having at least one HMF oligomer, for the reaction step.

13. The method according to claim 12, wherein the 5-hydroxymethylfurfural is provided by treating an aqueous suspension of cellulosic biomass and/or an aqueous carbohydrate solution of at least one hexose and/or an aqueous 5-hydroxymethylfurfural solution under hydrothermal conditions.

* * * * *